(12) United States Patent
Seufert (10) Patent No.: US 6,934,363 B2  
(45) Date of Patent: Aug. 23, 2005

(54) RADIATION DIAPHRAGM FOR AN X-RAY APPARATUS

(75) Inventor: Matthias Seufert, Oberreichenbach (DE)

(73) Assignee: Siemens Aktiengesellschaft, Münich (DE)

( * ) Notice: Subject to any disclaimer, the term of this patent is extended or adjusted under 35 U.S.C. 154(b) by 274 days.

(21) Appl. No.: 10/307,764

(22) Filed: Dec. 2, 2002

(65) Prior Publication Data

US 2003/0112924 A1 Jun. 19, 2003

(30) Foreign Application Priority Data

Dec. 18, 2001 (DE) .......................................... 101 62 256

(51) Int. Cl.[7] .................................................. G21K 1/04
(52) U.S. Cl. ........................ 378/160; 378/150; 378/147; 378/153
(58) Field of Search ............................... 378/160, 150, 378/147, 153, 145

(56) References Cited

U.S. PATENT DOCUMENTS

| 2,542,196 A | * | 2/1951 | Haupt | 378/153 |
|---|---|---|---|---|
| 4,027,167 A | * | 5/1977 | Pollermann | 378/153 |
| 4,246,488 A | * | 1/1981 | Hura | 378/151 |
| 4,389,730 A | * | 6/1983 | Cutter | 378/153 |
| 4,514,859 A | | 4/1985 | Holzermer | |
| 4,641,335 A | * | 2/1987 | Hahn | 378/153 |
| 4,766,603 A | * | 8/1988 | Okabe et al. | 378/152 |
| 5,396,533 A | | 3/1995 | Holzermer | |
| 5,396,534 A | * | 3/1995 | Thomas | 378/160 |
| 5,563,924 A | | 10/1996 | Winkelmann | |
| 6,036,362 A | * | 3/2000 | Schmitt | 378/206 |

FOREIGN PATENT DOCUMENTS

| DE | 34 39 355 | 4/1993 |
|---|---|---|
| DE | 34 36 866 | 10/1994 |
| DE | 42 42 835 | 10/1995 |

* cited by examiner

Primary Examiner—Craig E. Church  
Assistant Examiner—Irakli Kiknadze  
(74) Attorney, Agent, or Firm—Schiff Hardin LLP (57) ABSTRACT

A radiation diaphragm for an X-ray apparatus has an absorber element that can be swiveled around a swiveling axis for the variable limitation of a ray bundle. The swiveling axis is oriented transversely to the ray bundle. A swivel arm that can be swiveled around the swiveling axis and that carries the absorber element. The absorber element can comprise a curved shape. Such a radiation diaphragm allows an especially effective radiation dose limitation for the patient.

9 Claims, 6 Drawing Sheets

RADIATION DIAPHRAGM FOR AN X-RAY APPARATUS

BACKGROUND OF THE INVENTION

1. Field of the Invention

The present invention is directed to a radiation diaphragm for an X-ray apparatus of the type having a variable-position absorber element for adjustably limiting a ray bundle. The invention is also directed to an X-ray apparatus employing such a radiation diaphragm.

2. Description of the Prior Art

Radiation diaphragms for X-ray apparatuses are disclosed, for example, by German PS 42 42 835, German PS 42 29 321 and European Application 0 103 794. As absorber elements or diaphragm jaws, the radiation diaphragms of German OS 42 29 312 and European Application 0 103 794 have at least two diaphragm plates that are linearly adjustable relative to one another in pairs, a ray bundle having a rectangular cross-section of different sizes being able to be gated thereby. European Application 0 103 794 additionally discloses pivotable, triangular diaphragm plates that also allow the gating of a ray bundle having an approximately circular cross-section. To this end, the additional diaphragm plates are respectively pivoted around an axis that proceeds parallel to the middle axis of the ray bundle.

A computed tomography apparatus having a radiation diaphragm is disclosed in German OS 44 37 969. An X-ray fan beam is generated by the primary radiation diaphragm fashioned as slit a slot diaphragm. This fan beam determines the dose profile in the patient, and thus the slice thickness in the exposure. It thus also influences the dose stress on the patient and the intensity of the detector signal from which the image data are acquired. It is necessary to set different apertures of the primary radiation diaphragm for setting different slice thicknesses.

SUMMARY OF THE INVENTION

An object of the present invention is to provide a radiation diaphragm for an X-ray apparatus with which the dose limitation for the patient is improved.

This object is inventively achieved in a radiation diaphragm of the type initially described having a pivotable absorber element for adjustably limiting the ray bundle, with a swiveling axis around which the absorber element is pivoted being oriented transverse to the ray bundle.

The radiation diaphragm of the invention has the advantage that the intensity profile it generates in the patient plane is particularly sharp, i.e. it corresponds especially well to a rectangular profile. In other words, rays in the ray bundle that traverse only a shorter path through the absorber element compared to other rays of the ray bundle, but nonetheless penetrate the absorber element occur to only a slight extent. Radiation exiting the radiation diaphragm of the invention, is composed substantially only of rays that either pass the radiation diaphragm completely unattenuated, since they do not penetrate the absorber element at all, or rays that cover the maximum path through the absorber element and are completely attenuated. Due to the pivoting of the absorber element, an angle between marginal rays of the ray bundle and a leading or face side of the absorber element is nearly 0° for many rays, namely particularly given a very large diaphragm aperture as well. This is because that, due to the pivotability of the absorber element—representing a rotational movement—the position of the absorber element with respect to the focus of an X-ray tube of the X-ray apparatus can be optimally aligned. A "smearing" of the intensity profile produced by the radiation diaphragm due to marginal rays that have a pronounced inclination relative to the absorber element, as would occur given a linear advance of the absorber plates, is advantageously reduced to a non-disruptive degree or entirely avoided given the radiation diaphragm of the invention.

The radiation diaphragm of the invention can be optimized so that as many marginal rays of the ray bundle as possible pass an imaginary extension of a surface of the absorber element as perpendicularly as possible. In other words, all rays of the ray bundle that are at least partially influenced by the absorber element should strike the absorber element as perpendicularly as possible, so that an optimally high proportion of these rays must traverse the same path length, particularly the maximum path length, through the absorber element and are thus attenuated in the same way, particularly maximally.

The swiveling axis preferably is oriented perpendicularly with respect to a middle ray of the ray bundle, particularly with respect to a connecting axis between a tube focus and the patient, or perpendicularly with respect to a normal from the focus to the patient.

In a preferred embodiment, the swiveling axis at the side of the X-ray tube proceeds through a diaphragm housing. In particular, the swiveling axis is attached directly or optimally close to the wall of the diaphragm housing at the side of the X-ray tube. This achieves a swiveling arm length of the absorber element that is not very much shorter than the distance of the focus of the X-ray tube of the X-ray apparatus from the plane of the absorber element. The optimum course of the marginal rays of the ray bundle through the absorber element can be achieved to an especially high degree as a result.

For realizing the swivel motion, the radiation diaphragm includes a swivel arm that is pivotable around the swiveling axis to which the absorber element is secured, for example at the end side thereof. The swivel arm alternatively can be fashioned as a lever or articulation.

A rotatably seated eccentric for producing a swivel motion of the absorber elements preferably is present at the absorber element, for example an eccentrically seated shaft. The eccentric can be driven by a drive unit, preferably in steps and/or by arbitrary, desired angles.

The employment of an eccentric for generating a swivel motion of the absorber element has the advantage that a mechanically rugged radiation diaphragm that is also suited for especially high rotational velocities in a computed tomography apparatus—up to two or three revolutions per second—can be realized.

For example, the eccentric can act on the swivel arm.

A further advantage of employing an eccentric is that vibrations are largely avoided or are at least reduced compared to a drive of the absorber element that is based on a rod components.

In a preferred embodiment of the radiation diaphragm of the invention, the absorber element has a curved shape. The absorber element is curved either only along one axis, particularly in the longitudinal direction of the slit diaphragm of a computed tomography apparatus, or along two different spatial directions, preferably proceeding perpendicularly to the longitudinal direction of the slit diaphragm as well.

As a result, the advantage is achieved that a perpendicular passing of the absorber element, or its imaginary extension, can be achieved for an even greater number of marginal rays of the ray bundle in view of the aforementioned optimization. The ray bundle that the radiation diaphragm gates in the patient plane thus has an even sharper intensity curve in the edge region, so that the dose stress needed for the patient can be advantageously reduced even further.

In particular, the curvature is concave at the X-ray tube side

The radius of curvature of this curvature preferably equals the spacing of the tube focus from the absorber element or at least equals a swivel arm length of the absorber element.

In particular, the absorber element is fashioned shell-like.

DESCRIPTION OF THE PREFERRED EMBODIMENTS

Figure 1:
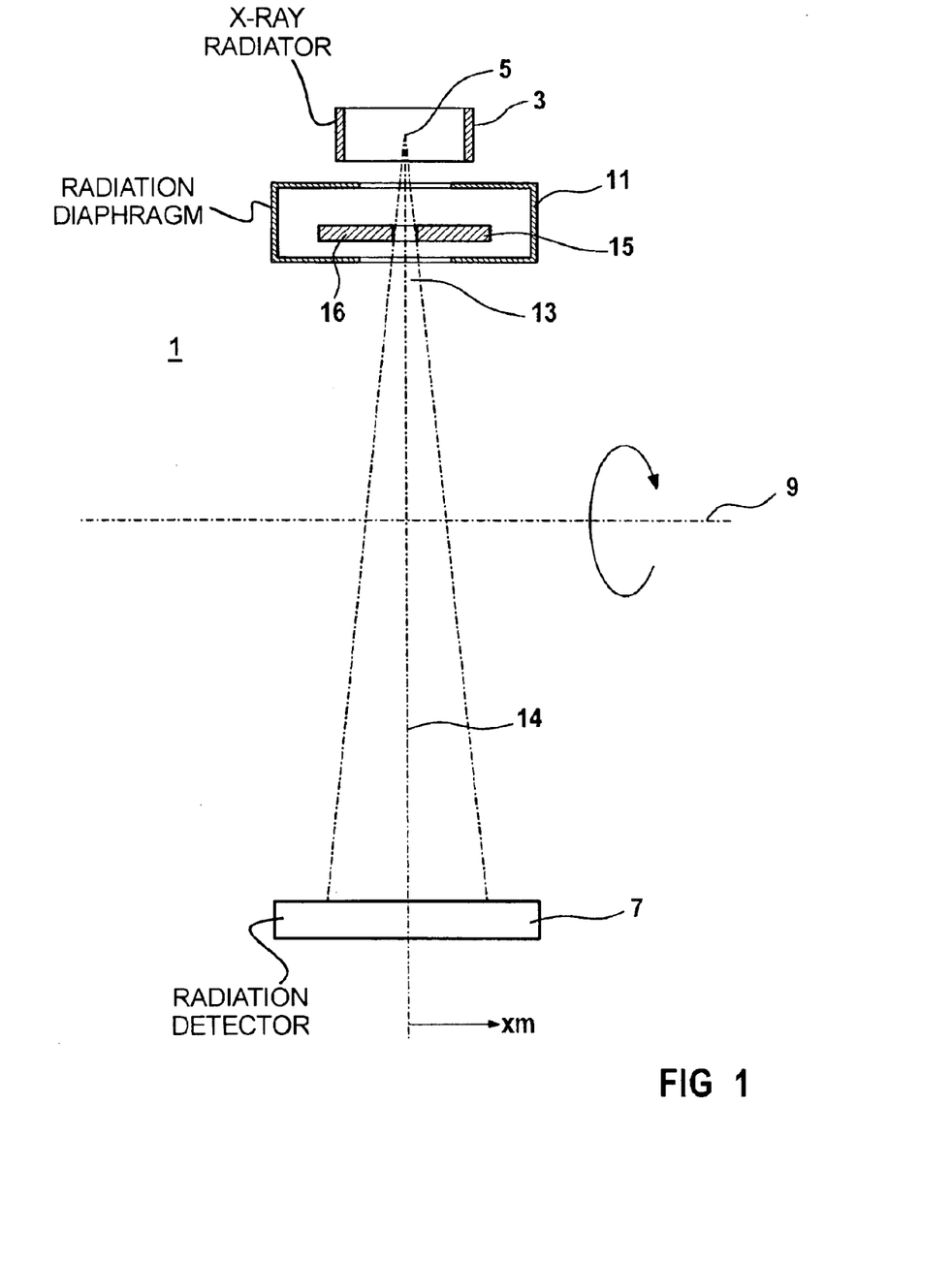
FIG. 1 is a schematic, overall view of an X-ray apparatus of the invention.

FIG. 1 shows an X-ray apparatus 1 fashioned as computed tomography apparatus, only the rotating part thereof having an X-ray radiator 3 with a focus 5, and a radiation detector 7, being shown. The X-ray radiator 3 and the detector 7 rotate around an axis 9. A radiation diaphragm 11 fashioned as primary radiation diaphragm generates a fan-shaped X-ray bundle 13 that transirradiates a patient (not shown) through whom the axis 9 passes. A middle ray of the X-ray bundle 13 is referenced 14.

The radiation diaphragm 11 rotates around the axis 9 together with the X-radiator 3 and the detector 7. A gantry that is present for the mechanical realization of the rotational motion is not explicitly shown, since this is well known. Given rotation of the components 3, 7, 11, the patient is transirradiated from different directions, and a computer calculates an image of the transirradiated part of the patient from the output signals of the detector 7. The fan plane proceeds perpendicularly to the plane of the drawing, and the detector 7 is composed of a row of individual detectors that likewise extends perpendicularly to the plane of the drawing. To this end, the detector 7 also is curved around the focus 5.

The radiation diaphragm 11 has diaphragm jaws or diaphragm plates functioning as absorber elements 15 and 16 respectively, and is only shown simplified in FIG. 1 and shall be explained in greater detail below with reference to FIGS. 2, 3 and 4.

Figure 2:
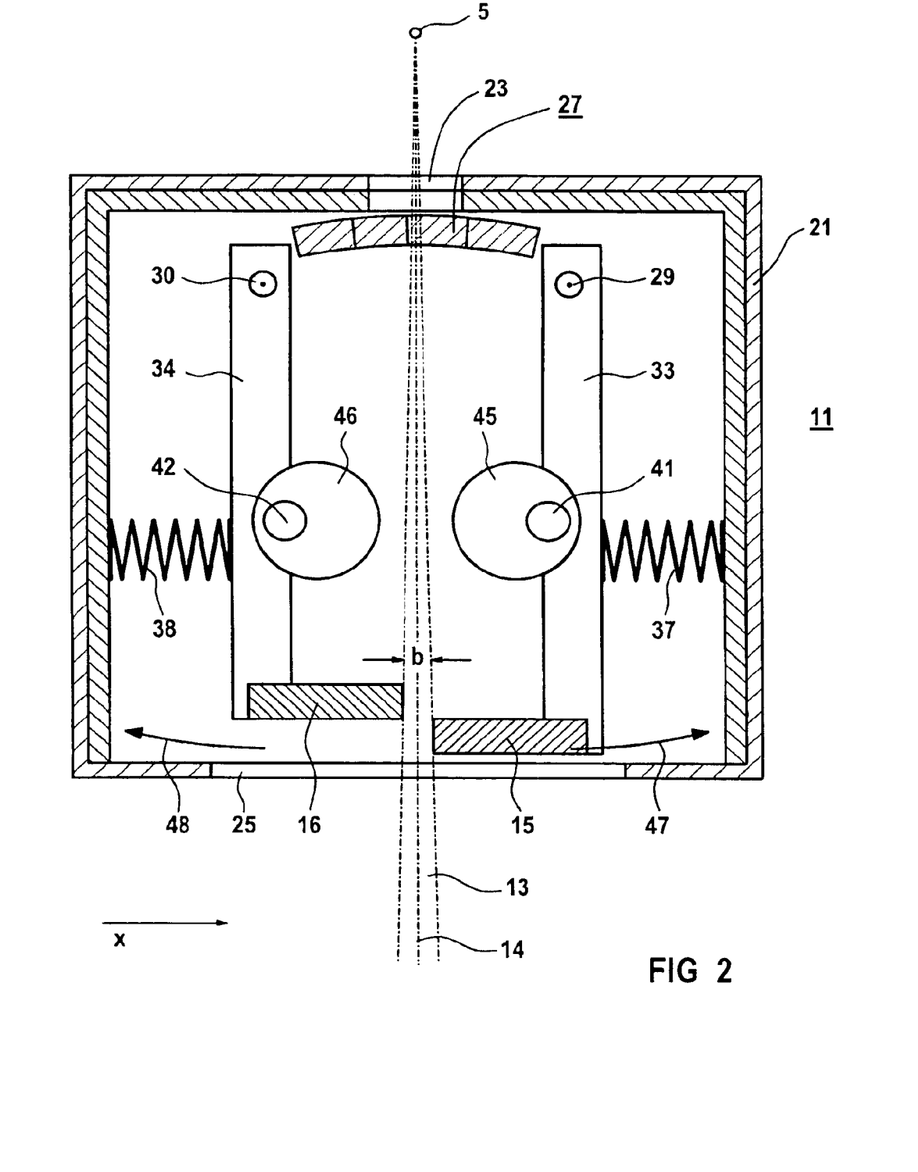
FIG. 2 is a cross-section of a first exemplary embodiment of a radiation diaphragm of the X-ray apparatus of FIG. 1.

FIG. 2 shows a cross-section of a first exemplary embodiment of a radiation diaphragm 11 of the X-ray apparatus of FIG. 1. The radiation diaphragm 11 has a diaphragm housing 21 with a focus-side entry aperture 23 and a larger exit aperture 25 at the opposite side of the diaphragm housing 21. X-rays emanating from the focus 5 of the X-ray 3 (see FIG. 1) first pass a spectral filter unit 27 arranged in the proximity of the entry aperture 23 and then pass the planar absorber elements 15, 16 arranged at the exit side insofar as the X-rays are not absorbed by these elements 15, 6 and thus are blanked. The rays passing the gap between the two plate-like or disk-like absorber elements 15, 16 form an X-ray fan beam that is required for the transirradiation of the patient in the computer tomography apparatus 1. Taking the imaging ratio into consideration, the gap width b defines the width of the desired X-ray radiation fan beam (in the x direction). The length of the X-ray radiation fan beam is influenced by the expanse of the absorber elements 15, 16 perpendicular to the plane of the drawing, i.e. in the longitudinal direction y of the slot diaphragm. This expanse amounts to approximately 20 cm.

The absorber elements 15, 16 are fabricated, for example, of lead, tungsten or tantalum.

The absorber elements 15, 16 are respectively secured to ends of swivel arms 33, 34 that can be respectively swiveled around swiveling axes 29, 30. The swiveling axes 29, 30, which are parallel to one another, proceed perpendicular to the plane of the drawing, i.e. perpendicular to an imaginary connecting line between the focus 5 and the patient. The swiveling axes 29, 30 thus are oriented transversely to the ray bundle 13, namely perpendicular with respect to the middle ray 14. The swivel arms 33, 34 have different lengths, so that—given a longer embodiment of the absorber elements 15, 16 than shown in FIG. 2—the radiation diaphragm 11 can also close gap-free ("ray-tight").

Respective spring elements 37, 38 that press the absorber elements 15, 16 toward the middle ray 14 are arranged between the diaphragm housing 21 and the respective swivel arms 33, 34. Without further measures, the radiation diaphragm 11 would remain in the closed condition as a result of these spring elements 37, 38.

Two eccentrics 45, 46 that are fashioned as eccentrically seated rollers and are seated at respective shafts 41, 42, are provided for opening the radiation diaphragm 11 and for varying the gap width b produced by it. The eccentrics 45, 46 engage respective round, curvature-matched recesses in the swivel arms 33, 34, having semicircular shape in the cross-section of FIG. 2. The eccentrics 45, 46 are driven by a stepping motor (not shown). With an increasing rotation of the eccentrics 45, 46 compared to the position shown in FIG. 2, the swivel arms 33, 34 are increasingly pressed toward the wall of the diaphragm housing 21, whereby the absorber elements 15, 16 execute the motion indicated with arrows 47, 48 and make the gap width b larger. The gap width b is variable from 0 through 15 mm.

Figure 3:
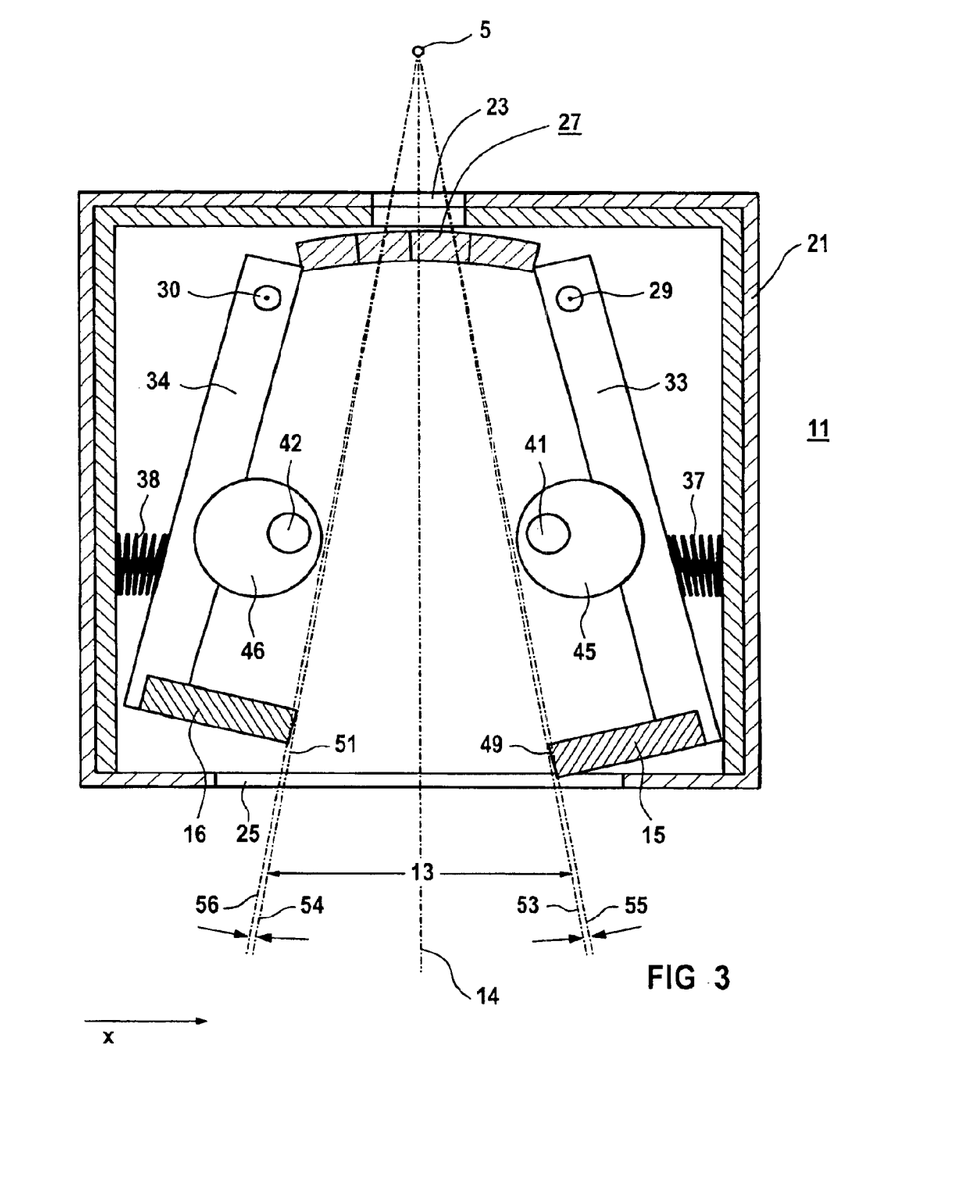
FIG. 3 shows the radiation diaphragm of FIG. 2 in a setting that is wide open.

FIG. 3 shows the radiation diaphragm 11 of FIG. 2 in a wide-open condition wherein the absorber elements 15, 16 have maximum excursion, i.e. wherein the spring elements 37, 38 are maximally compressed.

As a result of the swiveling axes 29, 30 being arranged as close as possible to the focus 5, an angle δ between the face ends or inner lateral surfaces 49, 51 of the rectangular absorber elements 15, 16 and a last unattenuated marginal ray 53, 54 is very small, particularly smaller than 5°. Marginal rays that lie even farther from the middle ray 14 are completely or partially blanked by the absorber element 15. That proportion of these marginal rays that are only partially attenuated or blanked is very slight. In order to illustrate this, marginal rays 55, 56 are also shown that proceed through the outer face edge of the absorber elements 15, 16 in the open position shown in FIG. 3. Marginal rays that lie even farther from the middle ray 14 than these marginal rays 55, 56 cover a distance in the absorber element 15, 16 that corresponds to the thickness thereof and thus are blanked completely or maximally. Only the marginal rays proceeding between the marginal rays 53 and 55, or 54 and 56, i.e. a negligible part, are only partly or less than maximally blanked by the absorber element 15, 16.

Figure 4:
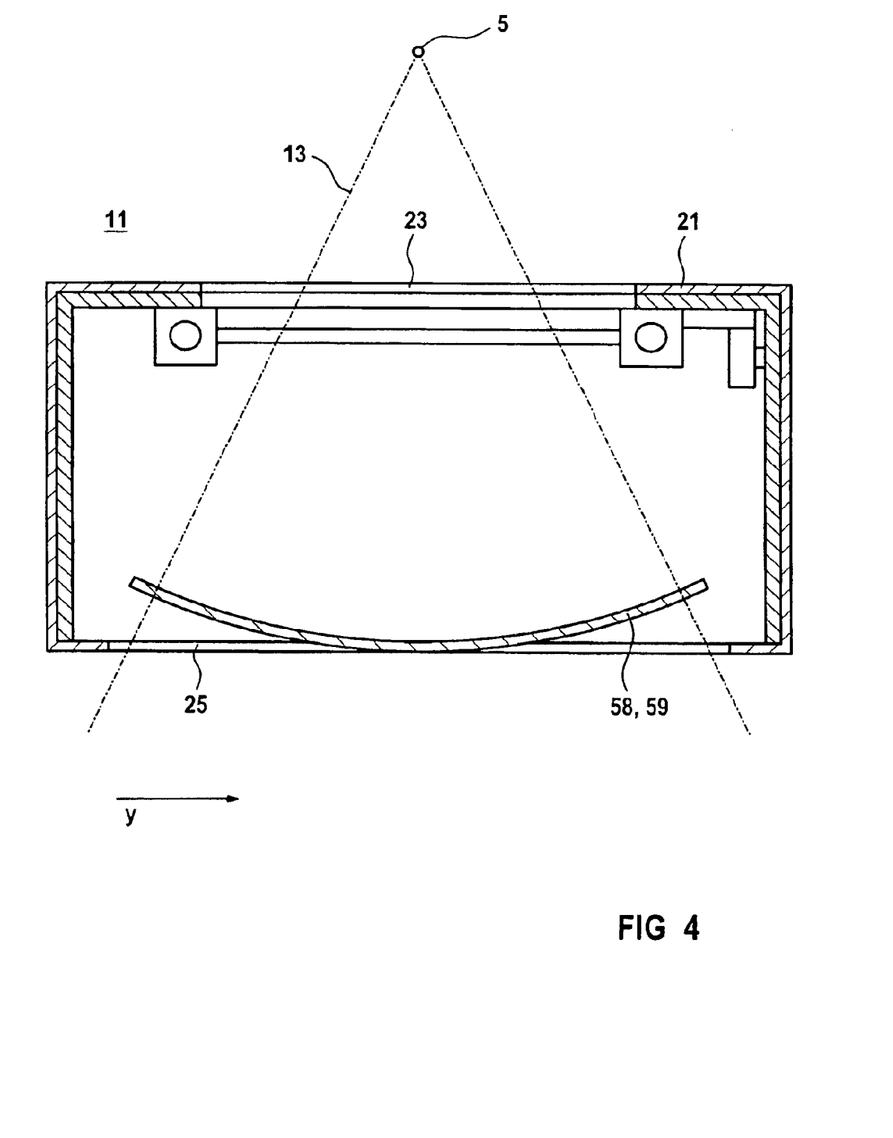
FIG. 4 is a cross-section of a second exemplary embodiment of a radiation diaphragm of the X-ray apparatus of FIG. 1.

The second exemplary embodiment of a radiation diaphragm 11 of the invention shown in FIG. 4 is mostly identical to the exemplary embodiment shown in FIGS. 2 and 3. However, the radiation diaphragm 11 of FIG. 4 differs in that the absorber elements 58, 59 have a shape that is curved in longitudinal direction y, whereby the curvature is concave toward the focus 5. The radius of curvature is equal to the distance from the focus 5 to the absorber elements 58, 59 (only one thereof is visible in FIG. 4). For clarity, all of the parts serving for the drive of the absorber elements 58, 59 are not shown in FIG. 4.

The absorber elements 58, 59 are fabricated, for example, of curved lead sheets or lead plates. The absorber elements 58, 59 are curved only in the longitudinal direction y. Their shape is that of a cylindrical shell.

Figure 5:
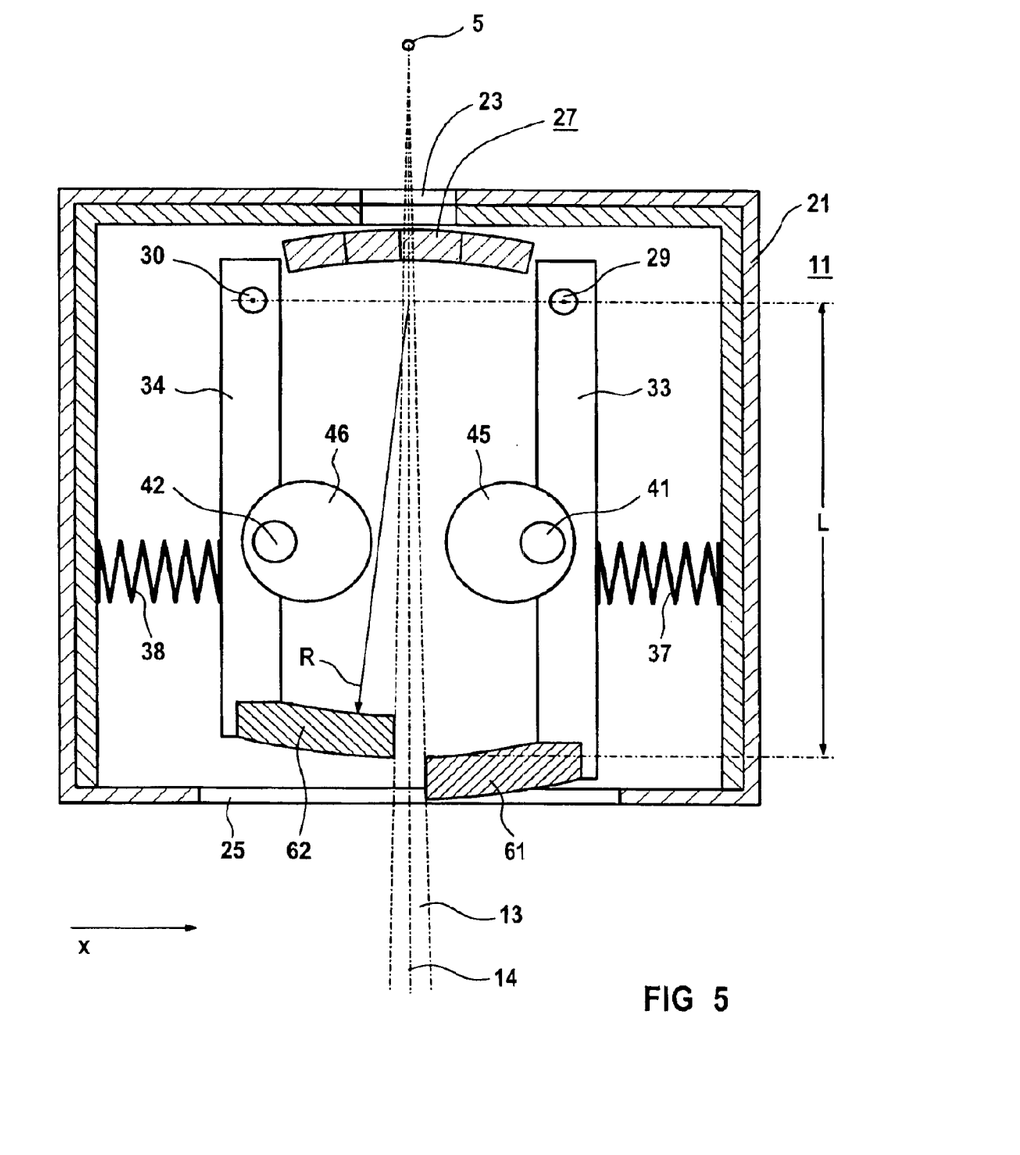
FIG. 5 is a cross-section of a third exemplary embodiment of a radiation diaphragm of the X-ray apparatus of FIG. 1.

The third exemplary embodiment of a radiation diaphragm 11 of the invention shown in FIG. 5 is likewise mostly identical to the exemplary embodiments shown in FIGS. 2 and 3. The radiation diaphragm 11 of FIG. 5, however, differs in that the absorber elements 61, 62 have a curved shape. The curvature of the absorber elements 61, 62 is concave toward the focus 5. A radius R of curvature for the curvature is of essentially the same size as a swivel arm length L that represents the effective lever length of the swivel arms 33, 34 for the absorber elements 61, 62, i.e. is essentially as large as the distance between the swivel axes 29, 30 and the absorber elements 61, 62.

In shape, the absorber elements 61, 62 represent a portion of a spherical shell that can be seen in cross-section in FIG. 4.

The employment of absorber element 61, 62 shaped like a spherical shell has the following advantage: In the exemplary embodiment shown in FIG. 3 and as a consequence of the approximately punctiform nature of the focus 5, the entered angle δ for marginal rays lying outside the plane of the drawing is larger than can be seen in FIG. 3. This effect is opposed by the curvature of the absorber elements 61, 62, so that a greater number of marginal rays optimally passes the absorber elements 61, 62.

Figure 6A:
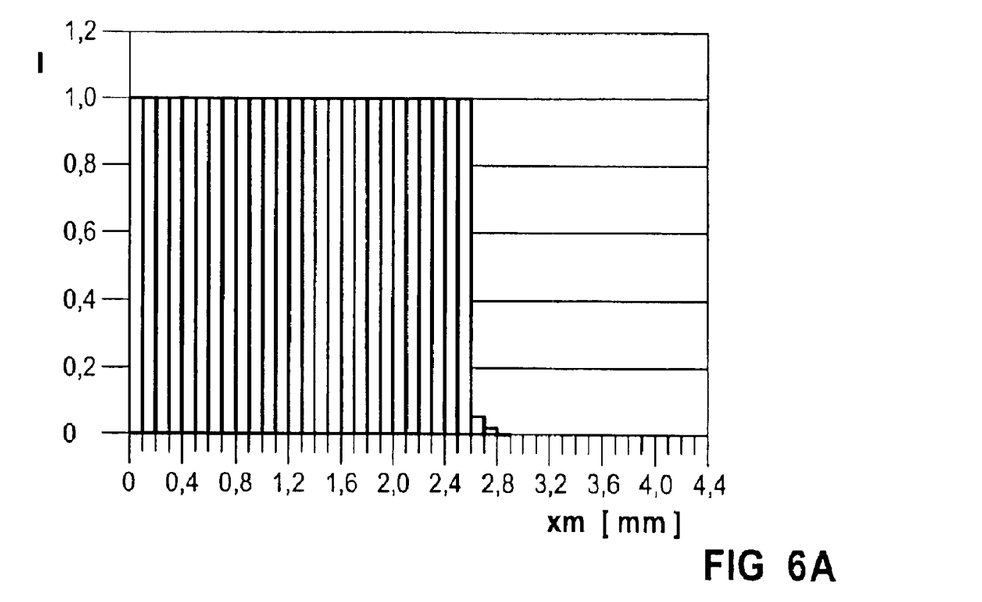
FIGS. 6A and 6B show the intensity curve of the X-ray bundle at the edge of the gated subject region obtained with a radiation diaphragm with linearly adjustable absorber element to the corresponding intensity curve obtained with a radiation diaphragm of the invention with pivotably adjustable absorber elements.
Figure 6B:
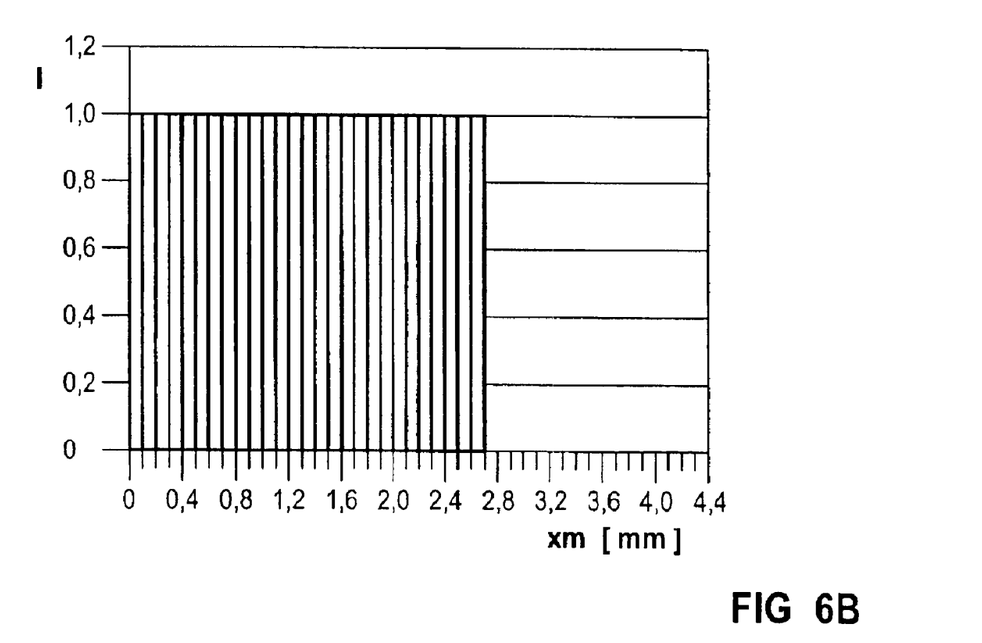

FIG. 6A shows the curve of the intensity I dependent on a center distance xm (see FIG. 1) for a known radiation diaphragm with linearly adjustable diaphragm jaws or diaphragm plates and GB shows such a curve for a radiation diaphragm 11 of the invention with pivotable, planar absorber jaws. The intensity is respectively normalized to 1.0.

Given conventional, linearly adjustable absorber jaws, the X-ray radiation—which proceeds from the focus of the X-ray tube—is attenuated or blanked in conformity with its path through the diaphragm jaws. When the jaws are opened, a non-perpendicular passage of X-rays arises at the edge of the diaphragm jaws due to the rectangular contour and the linear advance. Given large gap apertures, this results in an undesirable radiation gradient on the X-ray detector. This can be seen in FIG. 6A, particularly due to the unwanted radiation power in the range from 2.7 mm through 2.9 mm.

Given the pivotable diaphragm jaws according to the radiation diaphragm 11 of the invention, the angle δ between the jaw contour and the X-radiation is always nearly zero degrees, so that the gradient effect is minimized. This can be seen in FIG. 6B in that X-ray intensity I is no longer present in the range from 2.7 mm through 2.9 mm.

Also a part of the inventive contribution is the recognition that absorber elements 58, 59, 61, 62 that have a curved shape lead to a minimization of the dose stress on the patient, regardless of whether the absorber elements 58, 59, 61, 62 are pivotably seated. It is also advantageous in this context that the absorber element is not curved along two spatial directions x, y—as in the case of a spherical shell-like curvature—but only along one spatial direction y. Given a linearly adjustable absorber element with such a curved shape, the spatial direction along which the absorber elements are curved proceeds, for example, perpendicular to the plane of the drawing of FIGS. 2 through 4, if it is assumed that the linear adjustment motion would proceed in the same direction as the swivel motion accordingly FIGS. 2 through 4. Such a curvature of the absorber element as a sagging sheet or as a sagging plate can be seen, for example, in FIG. 4. The curvature proceeds along the longitudinal direction y of the rectangular ray fan that is gated.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray computed tomography apparatus comprising:
   an X-ray source for emitting X-rays in a ray bundle propagating in a propagation direction;
   a radiation detector on which said X-rays are incident;
   a rotating part on which said X-ray source and said radiation detector are mounted for rotating said X-ray source and said detector around a rotational axis at a rotational speed of multiple revolutions per second; and
   a radiation diaphragm attached to said rotating part between said X-ray source and said radiation detector, said radiation diaphragm comprising an absorber element composed of a material that attenuates said X-rays propagating in said propagation direction and a mounting arrangement to which said absorber element is mounted for pivoting said absorber element around a pivoting axis in said mounting arrangement, said pivoting axis being transverse to said propagation direction, including a rotatably seated eccentric for generating a swivel motion for pivoting said absorber element.

2. An X-ray computed tomography apparatus as claimed in claim 1 wherein said ray bundle has a center ray, and wherein said pivoting axis is disposed perpendicularly to said center ray.

3. An X-ray computed tomography apparatus as claimed in claim 1 further comprising a diaphragm housing having a radiation entry side at which said ray bundle enters said housing, and wherein said pivoting axis proceeds through said diaphragm housing at said radiation entry side.

4. An X-ray computed tomography apparatus as claimed in claim 1 wherein said mounting arrangement includes a swivel arm mounted for pivoting around said pivoting axis at one end, and having an opposite end at which said absorber element is mounted.

5. An X-ray computed tomography apparatus as claimed in claim 1 wherein said mounting arrangement includes a swivel arm mounted for pivoting around said pivoting axis at one end, and having an opposite end to which said absorber element is mounted, and wherein said eccentric acts on said swivel arm to generate said swivel motion.

6. An X-ray computed tomography apparatus as claimed in claim 1 wherein said absorber element has a curved shape.

7. An X-ray computed tomography apparatus as claimed in claim 6 having a diaphragm housing with a radiation entry side at which said ray bundle enters said housing, and wherein said absorber element has a concave curvature at a side facing said radiation entry side of said housing.

8. An X-ray computed tomography apparatus as claimed in claim 7 wherein said ray bundle emanates from a focus, and wherein said absorber element has a radius of curvature substantially equal to a distance of said focus from said absorber element.

9. An X-ray computed tomography apparatus as claimed in claim 6 wherein said absorber element has a shell-shape.

* * * * *